United States Patent
Ushijima et al.

(10) Patent No.: US 8,298,778 B2
(45) Date of Patent: Oct. 30, 2012

(54) METHOD AND KIT FOR DETECTING ANTIBODY TO AVIBACTERIUM PARAGALLINARUM

(75) Inventors: Toshihiro Ushijima, Aso (JP); Takashi Imamura, Kikuchi (JP); Ryuichi Sakamoto, Kikuchi (JP); Masashi Sakaguchi, Kikuchi (JP)

(73) Assignee: The Chemo-Sero-Therapeutic Research Institute, Kumamoto-shi (JP)

( * ) Notice: Subject to any disclaimer, the term of this patent is extended or adjusted under 35 U.S.C. 154(b) by 222 days.

(21) Appl. No.: 12/866,793

(22) PCT Filed: Feb. 6, 2009

(86) PCT No.: PCT/JP2009/052091
§ 371 (c)(1),
(2), (4) Date: Aug. 9, 2010

(87) PCT Pub. No.: WO2009/099204
PCT Pub. Date: Aug. 13, 2009

(65) Prior Publication Data
US 2011/0201034 A1 Aug. 18, 2011

(30) Foreign Application Priority Data
Feb. 8, 2008 (JP) ................................. 2008-029589

(51) Int. Cl.
*C07K 1/00* (2006.01)
*C07K 2/00* (2006.01)
*G01N 33/53* (2006.01)
*G01N 33/569* (2006.01)

(52) U.S. Cl. ........ 435/7.1; 435/7.32; 435/975; 530/300; 530/350

(58) Field of Classification Search .................. None
See application file for complete search history.

(56) References Cited

U.S. PATENT DOCUMENTS
6,544,519 B1 4/2003 Tokunaga et al.
2003/0027987 A1 2/2003 Tokunaga et al.

FOREIGN PATENT DOCUMENTS
| JP | 64-467 | 1/1989 |
| JP | 10-84969 | 4/1998 |
| JP | 2002-154983 | 5/2002 |
| JP | 2005-218414 | 8/2005 |
| WO | WO 98/12331 A1 | 3/1998 |

OTHER PUBLICATIONS

L. A. Page, Ph.D., "*Haemophilus* Infections in Cikens, I. Characteristics of 12 *Haemophilus* Isolates Recovered from Diseased Chickens", Am. J. Vet. Res., vol. 23, 1962, pp. 85-95.

Akira Sawato, et al., "Haemophilus Infections in Chickens 2. Types of *Haemophilus paragallinarum* Isolates from Chickens with Infectious Coryza, in Relation to *Haemophilus gallinarum* Strain No. 221", Jap. J. Vet Sci., vol. 40, 1978, pp. 645-652.

Katsumi Kume, DVM, PhD; et al., "Immunologic Relationship Between Page's and Sawata's Serotype of *Haemophilus paragallinarum*", Am. J. Vet. Res., vol. 41, No. 5, May 1980, pp. 757-760.

Akira Sawata, DVM, et al., "Biologic and Serologic Relationships Between Page's and Sawata's Serotypes of *Haemophilus paragallinarum*", Am. J. Vet. Res., vol. 41, Nov. 1980, pp. 1901-1904.

M. Matsumoto, et al., "A Broth Bacterin Against Infectious coryza: Immunogenicity of various Prepartions", Avian Dis., vol. 15, 1971, pp. 109-117.

H. Sun, et al., "A comparison of blocking ELISA and a haemagglutination inhibition assay for the detection of antibodies to avibacterium (*Haemophilus*) *paragallinarum* in sera from artificially infected chickens", Int. Ass. Bio., (IABS), vol. 25, 2007, pp. 317-320.

E. Tokunaga, et al., "Cloning of a gene encoding a protective antigen against infection from *Haemophilus paragallinarum* type A", Nippon Jui Gekkai Gakujutsu Shukai Koen Yoshishu, vol. $126^{th}$, PS50-4, 1998, p. 229 (with English Abstract).

T. Noro, et al., "Study of gene region encoding an antigen which is recognized by a monoclonal which has strong HI activity to *Haemophilus paragaillnarum* type A.", Nippon Jui Gakkai Gakujutsu Shukai Koen Yoshishu, vol. $139^{th}$, EP-193, 2005, pp. 212 (with English Abstract).

International Search Report issued Mar. 10, 2008, in PCT/JP2009/052091.

Extended Search Report issued Mar. 21, 2011 in International Application No. 09709287.8.

D. Miao, et al., "The development and application of a blocking ELISA kit for the diagnosis of infectious coryza", Avian Pathology, XP-002627348, vol. 29, 2000, pp. 219-225.

*Primary Examiner* — Albert Navarro
(74) *Attorney, Agent, or Firm* — Oblon, Spivak, McClelland, Maier & Neustadt, L.L.P.

(57) ABSTRACT

A method and a kit for detecting an antibody to *Avibacterium paragallinarum* are provided. A method for detecting an antibody to *Avibacterium paragallinarum* which comprises detecting an antibody induced by an outer-membrane protein of *Avibacterium paragallinarum* serotype A and/or serotype C by ELISA with a solid phase to which a peptide consisting of an amino acid sequence of non-homologous region of said outer-membrane protein or a portion thereof is immobilized, and a detection kit used for said method.

18 Claims, 4 Drawing Sheets

A.pg-A 1 3 0 4 A A ~ 1 3 3 4 A A (SEQ ID No:1   2 4 3 A A ~ 2 7 3 A A)

| I T G L V D V V K K | T N S P I T V E P S T D | S N K K K T F T V |

A. pg-C 1 1 0 0 A A ~ 1 1 3 0 A A (SEQ ID No:2   3 8 A A ~ 6 8 A A)

| I T G L V D V V K K | A N S P I T V E P S T D | N N K K K T F T V |

METHOD AND KIT FOR DETECTING ANTIBODY TO AVIBACTERIUM PARAGALLINARUM

CROSS-REFERENCE TO RELATED APPLICATIONS

The present application is a 35 U.S.C. §371 National Stage patent application of International patent application PCT/JP2009/052091, filed on Feb. 6, 2009, which claims priority to Japanese patent application JP 2008-029589, filed on Feb. 8, 2008.

TECHNICAL FIELD

The present invention relates to a method and a kit for detecting an antibody to *Avibacterium paragallinarum*. Specifically, the present invention relates to a method for detecting an antibody to *Avibacterium paragallinarum* (hereinafter also refer to as "A.pg"; previously referred to as *Haemophilus paragallinarum*) which comprises detecting an antibody induced by an outer-membrane protein (hereinafter also refer to as "HMT p210 polypeptide") of *Avibacterium paragallinarum* serotype A and/or serotype C by ELISA with a solid phase to which a peptide consisting of an amino acid sequence of non-homologous region of said outer-membrane protein or a portion thereof is immobilized, and a detection kit used for said method. Although a peptide is referred to as dipeptide, tripeptide, oligopeptide, polypeptide, and the like depending on the number of amino acid residues constituting of said peptide, a peptide as used herein is defined merely as "peptide" as encompassing any of these peptides.

BACKGROUND ART

Avian infectious coryza caused by infection with A.pg is known as important respiratory diseases in poultry. Poultry suffering from avian infectious coryza have a running nose, swelling of the face and epiphora as cardinal symptoms. Avian infectious coryza brings about a great economical damage since it leads to decrease in the breeding rate of poultry, retarding of egg laying, decrease in egg production or failure of egg laying.

Page et al. classified A.pg into three serotypes A, B and C (Non-patent reference 1) whereas Sawata et al. classified into two serotypes 1 and 2 (Non-patent reference 2). Subsequently, Kume et al. reported that serotype A by Page corresponds to serotype 1 by Sawata et al. whereas serotype C by Page corresponds to serotype 2 by Sawata et al. (Non-patent references 3 and 4). Nowadays, serotype A (serotype 1) of A.pg (hereinafter also refer to as "A.pg-A") and serotype C (serotype 2) of A.pg (hereinafter also refer to as "A.pg-C") are considered to be a main causative agent of avian infectious coryza.

For protection from avian infectious coryza, an inactivated vaccine has hitherto been used widely which is obtained by inactivating the cells of A.pg-A or A.pg-C with formalin, thimerosal, and the like. However, adverse side effects caused by such an inactivated vaccine has been an issue as it was reported that local necrotic lesions are formed in the inoculated chicken when the vaccine is administered (Non-patent reference 5), and hence, development of a highly safe vaccine is earnestly desired.

Under the circumstances, there have been developed or are under development a component vaccine where only a protective antigen, i.e. an effective component, obtained from bacterial cells or culture supernatant is used; a recombinant vaccine where a gene coding for a protective antigen is cloned by genetic recombination technique and expressed in bacteria, yeast, animal cells, plant cells, insect cells, and the like, and a product expressed in a large amount is purified and used; and a vector vaccine where a gene coding for a protective antigen is inserted into a viral vector, and the like.

For instance, Tokunaga et al. have successfully purified, from culture of A.pg-A, a polypeptide having about 130 kd of molecular weight from said A.pg-A, said polypeptide inducing production of a hemagglutination-inhibition antibody (HI antibody) and protecting against avian infectious coryza by A.pg-A (Patent reference 1). Furthermore, they have cloned a DNA fragment coding for said 130 Kd polypeptide and expressed said gene fragment in *E. coli* to find that the produced polypeptide could protect from avian infectious coryza caused by *Avibacterium paragallinarum* serotype A. Besides, they used said DNA fragment coding for the 130 Kd polypeptide as a probe to identify an HMT p210 gene coding for serotype A HMT p210 polypeptide, an outer-membrane protein having a hemagglutination activity, consisting of 2,042 amino acids. They also cloned from *Avibacterium paragallinarum* serotype C a DNA fragment hybridizable with said DNA fragment to obtain serotype C HMT p210 gene (Patent reference 2). They compared nucleotide sequences of open reading frame of HMT p210 genes of *Avibacterium paragallinarum* serotypes A and C to report that homology between both genes was about 80% as a whole, and that a region of about 3.4 kbp at the 5'-end (hereinafter refer to as "Region 1") and a region of about 1.2 kbp at the 3'-end (hereinafter refer to as "Region 3") had a very high homology while a region of about 1.5 kbp flanked by the two regions (hereinafter refer to as "Region 2") had a low homology (Patent reference 2).

It was also reported by Noro et al. that the HMT p210 gene discovered by Tokunaga et al. is important for a target region of a serotype specific vaccine. Noro et al. reported that, by immunizing poultry with a peptide encoded by a DNA fragment of from 4,801 bp to 5,157 bp, which is a portion of HMT p210 gene coding for the A.pg-A HMT p210 polypeptide, said peptide induced an HI antibody and had a vaccinal effect against A.pg-A (Patent reference 3). Noro et al. also reported in the 143rd Meeting of the Japanese Society of Veterinary Science held on Apr. 3-5, 2007, Japan that, by immunizing poultry with a peptide encoded by a DNA fragment of 5.5 kbp, which is a portion of HMT p210 gene coding for the A.pg-C HMT p210 polypeptide, said peptide induced an HI antibody and had a vaccinal effect against A.pg-C.

Serum diagnosis has not been performed for avian infectious coryza since, in addition to acute progress of the disease, poultry infected with A.pg are not likely to induce an antibody even after onset of the disease. On the other hand, poultry undergone vaccination induce an antibody to Hemagglutinin (hereinafter also referred to as "HA") on the surface of the A.pg cells and, for estimation of vaccinal effect in vitro, a hemagglutination-inhibition test (hereinafter also referred to as "HI test") with an anti-HA antibody has been performed. HI test, where fresh chicken erythrocytes or chicken erythrocytes fixed with glutaraldehyde are used, is indicated to have defects: (1) since fresh chicken erythrocytes are necessary for estimation of vaccinal effect of A.pg-A, it is troublesome and laborsome such as obtaining chickens for blood (breeding and managing chickens under condition of separation from pathogens), bleeding, blood treatment, and the like, (2) stable results are not likely to be obtained since the results may be influenced by the lots of chickens erythrocytes and estimation of an antibody titer is made by subjectivity of a person who measures.

On the other hand, Sun et al. reported, for alternative serum diagnostic of HI test, blocking ELISA (B-ELISA) using a serotype specific monoclonal antibody (Non-patent reference 6). B-ELISA is ELISA where serotype A or C cells disrupted by sonication were used as an antigen and monoclonal antibodies reactive with the respective serotypes were used to competitively detect antibodies in sera. This method is advantageous in that it has a higher sensitivity than HI test and may treat multiple antibodies. However, it requires four steps, i.e. addition of sera, addition of monoclonal antibodies, addition of anti-mouse IgG-HRP labeled antibody and addition of a substrate for development, one more step than in ordinary ELISA, rendering troublesome procedures. Also, for this method, serotype specific monoclonal antibodies need be obtained. For manufacturing a kit, it will take trouble of preparing and adding a plate immobilized with an antigen and reference serum as well as monoclonal antibodies. Besides, it is noted that said B-ELISA is a system that detects an antibody to only an antigenic epitope recognized by a single monoclonal antibody for the respective serotypes. With a system that detects an antibody to a single epitope, however, when said epitope is lost due to mutation of A.pg, it is highly liable not to detect its infection or an antibody induced by vaccination.

Patent reference 1: Japanese Patent Publication No. 10-84969
Patent reference 2: WO98/12331
Patent reference 3: Japanese Patent Publication No. 2005-218414
Non-patent reference 1: Am. J. Vet. Res., 23:85-95, 1962
Non-patent reference 2: Jpn. J. Vet. Sci., 40:645-652, 1978
Non-patent reference 3: Am. J. Vet. Res., 41:757-760, 1980
Non-patent reference 4: Am. J. Vet. Res., 41:1901-1904, 1980
Non-patent reference 5: Avian Dis., 15:109-117, 1971
Non-patent reference 6: Int. Ass. Bio. (IABS), 35:317-320, 2007

DISCLOSURE OF THE INVENTION

Technical Problem to be Solved by the Invention

An object of the present invention is to provide a method for detecting antibodies, distinctively antibodies to A.pg serotype A and to serotype C, respectively. Specifically, a method for detecting antibodies is provided that is characterized by using a recombinant antigenic peptide with which antibodies to A.pg serotype A and to serotype C, respectively, may be distinguished from each other. More specifically, a method for detecting antibodies is provided that is characterized by using a recombinant antigenic peptide comprising an amino acid sequence within a region having low homology between outer-membrane proteins of A.pg serotype A and serotype C.

Means for Solving the Problems

Under the circumstances, the present inventors have assiduously investigated so as to attain the objects mentioned above, and as a result, have found that an amino acid sequence homologous between A.pg-A and A.pg-C is included in the amino acid sequence of Region 2, as separately located, of p 210 polypeptide encoded by HMT p210 gene, an important vaccinal antigen, (among 31 amino acid residues of amino acids Nos. 243-273 of SEQ ID NO: 1 for A.pg-A and of amino acids Nos. 38-68 of SEQ ID NO: 2 for A.pg-C, 29 amino acid residues are identical; cf. FIG. 3), and that said amino acid sequence forms an epitope. Besides, the present inventors have found that an amino acid sequence highly homologous between A.pg-A and A.pg-C is included in a portion of Region 2 as defined by Tokunaga et al. Thus, for HMT p210 polypeptides for A.pg-A and A.pg-C, the present inventors have prepared peptides that do not include the above two homologous amino acid sequences and used said peptides for ELISA with a microtiter plate where said peptides are immobilized for measurement of antibodies. As a result, it was proved that antibodies induced by a vaccine from A.pg-A and a vaccine from A.pg-C, respectively, could specifically be distinguished from each other, to thereby complete the present invention.

Thus, the present invention includes the followings:
(1) A method for detection of an antibody to *Avibacterium paragallinarum* characterized by that said method comprises antibody measurement by reacting at least one antigen of Peptide A or Peptide B below with a sample:
Peptide A:
which is a peptide which consists of a portion of the amino acid sequence of SEQ ID NO: 1, consists of a peptide chain of 6 or more amino acid residues, and does not include an amino acid sequence of amino acids Nos. 243-273 of SEQ ID NO: 1;
Peptide B:
which is a peptide which consists of a portion of the amino acid sequence of SEQ ID NO: 2, consists of a peptide chain of 6 or more amino acid residues, and does not include an amino acid sequence of amino acids Nos. 38-68 of SEQ ID NO: 2.
(2) The method for detection of (1) above wherein Peptide A or Peptide B is a peptide chain of 10 or more amino acid residues.
(3) The method for detection of (1) above wherein Peptide A or Peptide B is a peptide chain of 20 or more amino acid residues.
(4) The method for detection of (1) above wherein Peptide A or Peptide B is a peptide chain as follows:
Peptide A:
which is a peptide which consists of a portion of the amino acid sequence of SEQ ID NO: 1, comprises an amino acid sequence of amino acids Nos. 8-236 of SEQ ID NO: 1, and does not include an amino acid sequence of amino acids Nos. 243-273 of SEQ ID NO: 1;
Peptide B:
which is a peptide which consists of a portion of the amino acid sequence of SEQ ID NO: 2, comprises an amino acid sequence of amino acids Nos. 69-452 of SEQ ID NO: 2, and does not include an amino acid sequence of amino acids Nos. 38-68 of SEQ ID NO: 2.
(5) The method for detection of (1) above wherein Peptide A or Peptide B is a peptide chain as follows:
Peptide A:
which is a peptide consisting of an amino acid sequence of amino acids Nos. 8-236 of SEQ ID NO: 1;
Peptide B:
which is a peptide consisting of an amino acid sequence of amino acids Nos. 69-452 of SEQ ID NO: 2.
(6) The method for detection of (4) above wherein Peptide A is a peptide chain as follows:
Peptide A:
which is a peptide which consists of a portion of the amino acid sequence of SEQ ID NO: 1, comprises an amino acid sequence of amino acids Nos. 274-445 of SEQ ID NO: 1, and does not include an amino acid sequence of amino acids Nos. 243-273 of SEQ ID NO: 1.
(7) The method for detection of (5) above wherein Peptide A is a peptide chain as follows:
Peptide A:
which is a peptide consisting of an amino acid sequence of amino acids Nos. 274-445 of SEQ ID NO: 1.

(8) The method for detection of any of (1) to (7) above wherein Peptide A or Peptide B is a peptide having an amino acid sequence wherein 1 or several amino acid residues therein are deleted, added or substituted.
(9) The method for detection of any of (1) to (8) above wherein the antibody measurement is selected from the group consisting of ELISA, Western blot and dot blot.
(10) The method for detection of any of (1) to (9) above wherein the sample is sera from chickens infected with *Avibacterium paragallinarum* or sera from chickens to which *Avibacterium paragallinarum* vaccine is administered.
(11) A kit for measurement of an antibody to *Avibacterium paragallinarum* characterized by that at least one of Peptide A or Peptide B below is used as an antigen:
Peptide A:
which is a peptide which consists of a portion of the amino acid sequence of SEQ ID NO: 1, consists of a peptide chain of 6 or more amino acid residues, and does not include an amino acid sequence of amino acids Nos. 243-273 of SEQ ID NO: 1;
Peptide B:
which is a peptide which consists of a portion of the amino acid sequence of SEQ ID NO: 2, consists of a peptide chain of 6 or more amino acid residues, and does not include an amino acid sequence of amino acids Nos. 38-68 of SEQ ID NO: 2.
(12) The kit for measurement of an antibody of (11) above wherein Peptide A or Peptide B is a peptide chain of 10 or more amino acid residues.
(13) The kit for measurement of an antibody of (11) above wherein Peptide A or Peptide B is a peptide chain of 20 or more amino acid residues.
(14) The kit for measurement of an antibody of (11) above wherein Peptide A or Peptide B is a peptide chain as follows:
Peptide A:
which is a peptide which consists of a portion of the amino acid sequence of SEQ ID NO: 1, comprises an amino acid sequence of amino acids Nos. 8-236 of SEQ ID NO: 1, and does not include an amino acid sequence of amino acids Nos. 243-273 of SEQ ID NO: 1;
Peptide B:
which is a peptide which consists of a portion of the amino acid sequence of SEQ ID NO: 2, comprises an amino acid sequence of amino acids Nos. 69-452 of SEQ ID NO: 2, and does not include an amino acid sequence of amino acids Nos. 38-68 of SEQ ID NO: 2.
(15) The kit for measurement of an antibody of (11) above wherein Peptide A or Peptide B is a peptide chain as follows:
Peptide A:
which is a peptide consisting of an amino acid sequence of amino acids Nos. 8-236 of SEQ ID NO: 1;
Peptide B:
which is a peptide consisting of an amino acid sequence of amino acids Nos. 69-452 of SEQ ID NO: 2.
(16) The kit for measurement of an antibody of (14) above wherein Peptide A is a peptide chain as follows:
Peptide A:
which is a peptide which consists of a portion of the amino acid sequence of SEQ ID NO: 1, comprises an amino acid sequence of amino acids Nos. 274-445 of SEQ ID NO: 1, and does not include an amino acid sequence of amino acids Nos. 243-273 of SEQ ID NO: 1.
(17) The kit for measurement of an antibody of (15) above wherein Peptide A is a peptide chain as follows:
Peptide A:
which is a peptide consisting of an amino acid sequence of amino acids Nos. 274-445 of SEQ ID NO: 1.
(18) The kit for measurement of an antibody of any of (11) to (17) above wherein Peptide A or Peptide B is a peptide having an amino acid sequence wherein 1 or several amino acid residues therein are deleted, added or substituted.
(19) The kit for measurement of an antibody of any of (11) to (18) above wherein the antibody measurement is selected from the group consisting of ELISA, Western blot and dot blot.
(20) The kit for measurement of an antibody of any of (11) to (19) above wherein the sample is sera from chickens infected with *Avibacterium paragallinarum* or sera from chickens to which *Avibacterium paragallinarum* vaccine is administered.

More Efficacious Effects than Prior Art

In accordance with the present invention, a method and a kit for detecting an antibody to *Avibacterium paragallinarum* are provided. The peptides from A.pg-A and from A.pg-C as used herein do not include an amino acid sequence homologous to each other and therefore may specifically bind to an antibody induced by a vaccine from A.pg-A and an antibody induced by a vaccine from A.pg-C, respectively. Accordingly, a method and a kit for detection of the present invention enables to distinctly measure an antibody titer for the respective antibodies to vaccines from A.pg-A and A.pg-C in chicken sera not only when the respective vaccines are separately administered to chickens but also when a mixture of the vaccines is administered.

Furthermore, the present invention, as using a purified recombinant antigen, allows for immobilization of a higher concentration of an antigen than the prior art using cell debris of A.pg and hence allows for construction of a system for measuring an antibody with higher detection sensitivity. The method for detecting an antibody of the present invention, as using the antigenic peptide which is capable of distinguishing a serotype of A.pg, detects an antibody more simply and, in view of antigenic mutation of A.pg, more reliably than B-ELISA using a serotype specific monoclonal antibody.

Besides, by the method for detection of the present invention, antibodies are distinguished not only in chicken sera after vaccination but also in sera from chickens infected with A.pg.

Figure 1:
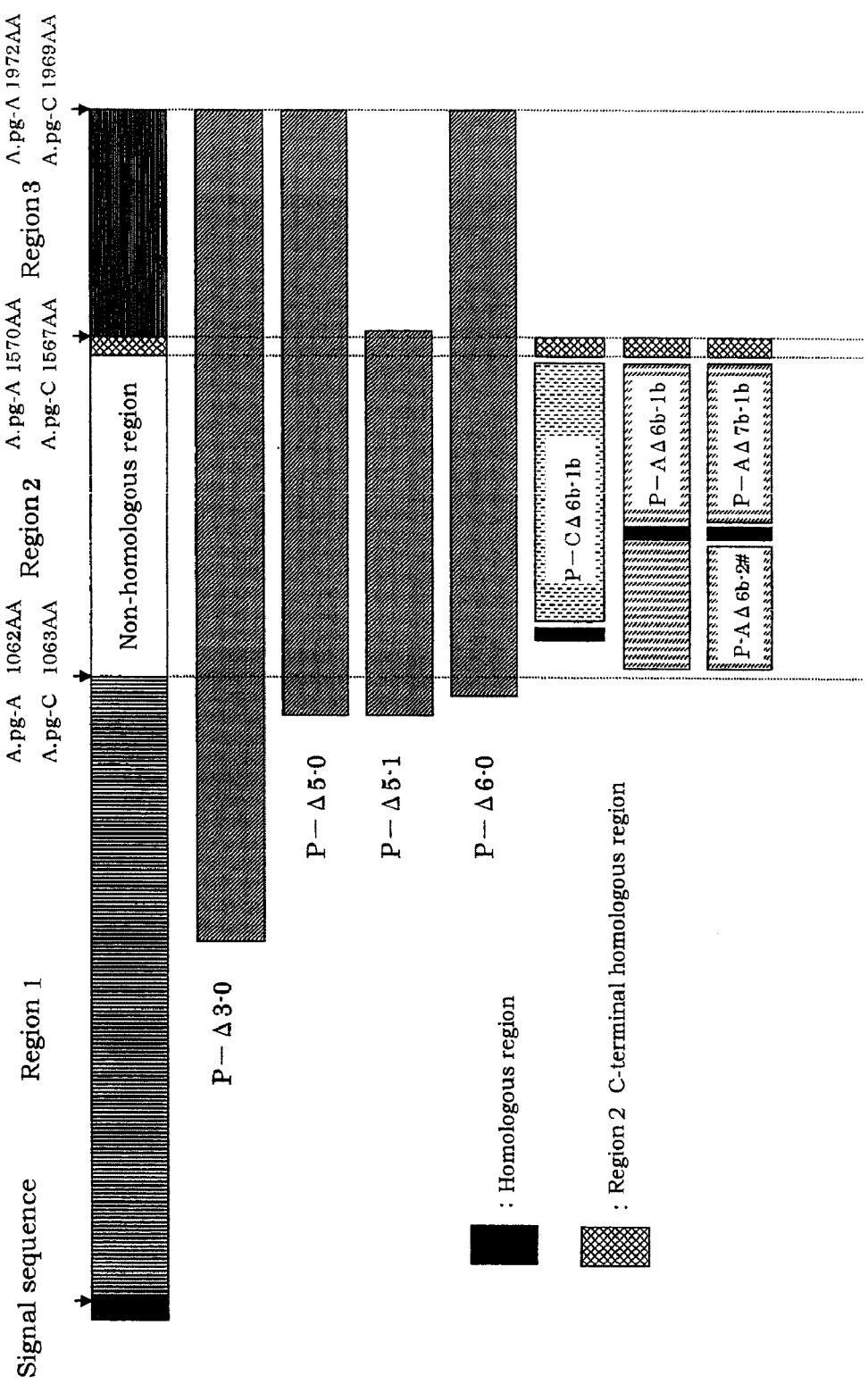
FIG. 1 shows HMT p210 polypeptide and its fragments with positional relationship thereof. Portions filled in black show a homologous sequence in Region 2 whereas meshed portions show a C-terminal homologous sequence in Region 2. The numbering of amino acid sequence in the figure corresponds to that of SEQ ID NO: 1 (A.pg-A) and of SEQ ID NO: 5 (A.pg-C) disclosed in Patent reference 2.

1b as an antigen and protection from onset of disease after challenge with A.pg-C. In the figure, ● shows chickens without onset of disease whereas ○ shows chickens with onset of disease.

BEST MODE FOR CARRYING OUT THE INVENTION

The present invention is characterized by a method and a kit for detection of an antibody to *Avibacterium paragallinarum* by antibody measurement using as an antigen peptides obtained by removing a homologous amino acid sequence between A.pg-A and A.pg-C slightly present in a non-homologous region of the amino acid sequence encoded by A.pg-derived HMT p210 gene.

For the method for detection of an antibody to *Avibacterium paragallinarum* of the present invention, a non-homologous region or a portion thereof of the amino acid sequence encoded by A.pg-A- and/or A.pg-C-derived HMT p210 gene is used as an antigen. A non-homologous region as used herein is defined as a region of about 1.3 kbp (SEQ ID NO: 1 for A.pg-A and SEQ ID NO: 2 for A.pg-C) which is obtained by removing a homologous sequence at the C-terminal from the amino acid sequence encoded by a DNA region of about 1.5 kbp (Region 2) flanked by the amino acid sequence encoded by a DNA region of about 3.4 kbp (Region 1) at the 5'-end and the amino acid sequence encoded by a DNA region of about 1.2 kbp (Region 3) at the 3'-end (cf. FIG. 1). A gene coding for the amino acid sequence of the non-homologous region is hereinafter referred to as "A.pg-1.3 gene" or is also referred to as "A.pg-A1.3 gene" and "A.pg-C1.3 gene" for distinction between A.pg-A and A.pg-C.

For three A.pg-A strains (221 strain, 053 strain and W strain) isolated from A.pg-infected chickens, the nucleotide sequence corresponding to a non-homologous region of HMT p210 gene is perfectly consistent between 053 strain and W strain and differs only one nucleotide between these two strains and 221 strain. On the other hand, for three A.pg-C strains (53-47 strain, Modest strain and NK-1 strain), said nucleotide is such that Modest strain and NK-1 strain had deletion of 3 nucleotides (1 amino acid) as compared to 53-47 strain. Accordingly, it may be said that a non-homologous region of the same serotype is highly conserved and thus any strain of the same serotype may be used for the present invention.

An A.pg-1.3 gene and a DNA fragment containing said gene may be obtained as described below. For growth of A.pg, a culture medium may be used which appropriately contains polypeptone, glucose, casamino acid, sodium glutamate, yeast extract, sodium chloride, chicken broth, βNAD, chicken serum, and the like. For the present invention, a broth supplemented with chicken serum, containing 5 g polypeptone, 1 g casamino acid, 5 g sodium chloride, 5 g sodium L-glutamate, 1 g glucose, 10 g yeast extract, 175 mL chicken broth, 25 mL chicken serum and 0.025% nicotineamide adenine dinucleotide (β-NAD) in 1000 mL culture medium, was used for growth of a small to medium amount of the cells. Culture condition may be set at the temperature 37° C. and the duration in a range of 16-24 hours but may suitably be adjusted depending on the purpose of use, the format of culture, the amount of cells inoculated, the scale of culture medium, and the like.

The cells in culture may be recovered in a precipitate by centrifuge (8,000 rpm, 20 minutes). An HMT p210 gene may be prepared, using as a starting material a whole RNA, mRNA or a genomic DNA extracted from the cells, by a general genetic recombination technique as taught by Sambrook et al. (Molecular Cloning, A Laboratory Manual Second Edition. Cold Spring Harbor Laboratory Press, N.Y., 1989). In practice, a commercially available kit may be used. For instance, reagents such as TRIzol reagent (Invitrogen), ISOGEN (NIPPON GENE CO., LTD.), StrataPrep Total RNA Purification Kit (TOYOBO) for extraction of RNA, SepaGene kit (Sanko Junyaku Co., Ltd.), ISOPLANT (Wako Pure Chemical Industries, Ltd.) for extraction of chromosomal DNA, a kit such as mRNA Purification Kit (Amersham Bioscience), Poly(A) Quick mRNA Isolation Kit (TOYOBO), mRNA Separator Kit (Clontech) for purification of mRNA, SuperScript plasmid system for cDNA synthesis and plasmid cloning (Invitrogen), cDNA Synthesis Kit (TAKARA SHUZO CO., LTD.), SMART PCR cDNA Synthesis & Library Construction Kits (Clontech), Directionary cDNA Library Construction systems (Novagen Inc.), GeneAmp PCR Gold (Applied Biosystems) for conversion into cDNA may be used.

More specifically, a chromosomal DNA may be extracted from cells recovered by centrifuge, using SepaGene kit (Sanko Junyaku Co., Ltd.), and the like, cleaved with an adequate restriction enzyme, preferably EcoRI, inserted into a commercially available cloning vector, e.g. λgt11; New England Biolabs (NEB) to prepare a DNA library. Using the obtained DNA fragments as a template, PCR may be performed to amplify DNA fragments in various sizes using, LA Taq (TAKARA BIO Inc.) in accordance with protocol attached thereto. Primers for use in PCR may be designed based on the nucleotide sequences of A.pg-A- and A.pg-C-derived HMT p210 genes as Tokunaga et al. disclosed (Patent reference 1). Primers for PCR may be readily available if asked to DNA synthesis contractor services (e.g. Sigma Genosys Japan K.K.). When designed, nucleotide sequences of appropriate restriction enzyme cleavage sites may be added at the 5'-end of upstream Primer and at the 5'-end of downstream Primer. Products amplified by PCR may be cloned into a gene cloning vector, pCR-XL-TOPO (Invitrogen) to prepare plasmid pCRDNT into which various DNA fragments are inserted. A nucleotide sequence of the obtained DNA fragments, after cloned into pBluescript II SK+ (Stratagene) or pCR2.1-TOPO (Invitrogen), may be determined with a DNA sequencer (ABI Prism 377; Applied Biosystems).

As described below, insofar that sensitivity is not decreased or non-specific reaction is not increased, a peptide to which amino acid mutation is introduced may be used as an antigen for the antibody measurement in the present invention. For introducing mutation at a specific amino acid in a peptide, site-directed mutagenesis may usually be employed where mutation is introduced to a nucleotide sequence of a DNA fragment coding for said peptide. In practice, site-directed mutagenesis may be performed with commercially available kits in which this technique is applied, such as Site-Directed Mutagenesis System (Mutan-Super Express Km, Mutan-Express Km, Mutan-K, and the like) by Takara, QuickChange Multi Site-Directed Mutagenesis Kit, QuickChange XL Site-Directed Mutagenesis Kit by Stratagene, GeneTailor Site-Directed Mutagenesis System by Invitrogen, in accordance with protocol attached thereto.

For obtaining DNA fragments coding for an amino acid sequence of various peptides that do not contain an amino acid sequence homologous between A.pg-A and A.pg-C, so that the homologous sequence as described above would not be contained, an ordinary PCR may be performed using primers designed from non-homologous region (the nucleotide sequence depicted in SEQ ID NO: 3 for A.pg-A and the nucleotide sequence depicted in SEQ ID NO: 4 for A.pg-C) and the A.pg-1.3 gene and a DNA fragment comprising the gene as a template. In case of a short amino acid sequence, its DNA fragment may also be prepared by artificial synthesis. The DNA fragments and the primers prepared in the present invention are shown in Table 1.

The thus obtained DNA fragments may be incorporated into an appropriate expression vector, which may then be introduced into a host for expression of each of the DNA fragments. For an expression vector, pQE30 (QIAGEN) or pET22b (Novagen Inc. or TAKARA BIO Inc.), and the like may be used, as appropriately selected. For expression of a heterologous protein or peptide, bacteria, yeasts, animal cells, plant cells, insect cells, and the like may normally be used, as appropriately selected depending on the purpose of use. For transformation of a host cell, methods known in the art may be used. For instance, calcium phosphate, DEAE dextran, approach using liposome of lipofectin, polyethylene glycol fusion of protoplast, electroporation, and the like may be used, as appropriately selected depending on a host cell as used. For expression of each of the DNA fragments of the present invention, E. coli may be used which allows for expression in a large amount. For expression in E. coli, various expression vectors having trp promoter, T7 promoter, cspA promoter, and the like have been developed and commercially available and may be used as appropriate. Depending on an expression vector, suitable E. coli such as BL21, HMS174, DH5α, HB101, JM109, and the like may be selected as a host. Transformation of E. coli may be conducted using commercially available competent cells in accordance with protocol attached thereto. Thus, recombinant E. coli producing the desired polypeptide may be obtained. For culture medium (e.g. LB, SOC, SOB, and the like) used for culture of E. coli, reagents used for selection of transformant (e.g. ampicillin) and reagents used for induced expression (e.g. indole acetic acid (IAA), isopropylthio-β-D-galactoside (IPTG), and the like), commercially available ones may be used. A pH of a culture medium may be within a range suitable for growth of E. coli (pH 6 to 8).

Screening of recombinant E. coli expressing a desired peptide (the object) may be carried out as described below. Cells cultured and grown in the presence of an expression inducer (IPTG was used in an expression system in the present invention) are collected by centrifuge (10,000 rpm, 5 minutes), suspended in a fixed volume of distilled water, disrupted by sonication or a homogenizer such as French press or Manton Golin and subject to centrifuge (15,000 rpm, 15 minutes) for separation and recovery in precipitate or supernatant. To distilled water may appropriately be added a surfactant (e.g. Triton X 100), a chelating agent (e.g. EDTA), liposome, and the like. A fixed amount of expressed products recovered in supernatant and precipitate may be subject to SDS-polyacrylamide gel electrophoresis, and after staining with Coomassie Brilliant Blue, expression of the object may be confirmed by a molecular size and stained image. For confirmation (or detection) of the object, approach based on an antigen-antibody reaction such as ELISA, Western blot, dot blot, and the like may also be used other than approach based on a molecular size as described above. All of these approaches are commonly used for detecting a heterologous protein or polypeptide expressed in E. coli and may be selected as appropriate.

For purifying the object from recombinant E. coli, a combination of the methods commonly used in the field of protein chemistry may be used such as e.g. centrifuge, salting-out, ultrafiltration, isoelectric focusing, electrophoresis, ion exchange chromatography, gel filtration chromatography, affinity chromatography, hydrophobic chromatography, hydroxyapatite chromatography, and the like. An amount of the obtained protein or polypeptide may be measured with a reagent for protein measurement such as BCA Protein Assay Reagent Kit (Pierce Biotechnology, Inc), Protein Assay Kit (BIO-RAD, Inc), and the like.

To facilitate purification of the object, it may be expressed in a fusion with other polypeptide or peptide. A vector for expressing such a fusion protein includes His-tag expression system (Novagen Inc.) which allows for addition of oligohistidine, a system capable of expression of a fusion protein with FLAG tag (Sigma), GST fusion protein purification system (Amersham Pharmacia) which allows for production of a fusion protein with glutathione S-transferase (GST), Magne-His Protein Purification System (Promega), and the like. For instance, as carried out in the working examples of the invention, after expression as a fusion protein with oligohistidine, a polypeptide of interest may be specifically purified with nickel affinity column (GE Healthcare Bioscience).

The thus obtained various peptides not containing a homologous amino acid sequence between A.pg-A and A.pg-C may be used in antibody measurement for detection of an antibody induced by avian infectious coryza vaccine or for serological diagnosis of A.pg-infected chickens. Specifically, antibody measurement such as ELISA, Western blot, dot blot, and the like may be applied. In case that many antibodies are to be handled, ELISA with a microtiter plate to which peptides are immobilized may preferably be used.

For a peptide to be immobilized to a microtiter plate, a peptide consisting of a non-homologous region in the amino acid sequence encoded by A.pg-1.3 gene, or a portion of said peptide, may be used. Since it is established that 6 to 10 or thereabout amino acids may form an epitope recognizable by an antibody (it is published on-line (http://www.genosys.jp/products/spots/spots_faq.html) that 3 to 6 amino acids are sufficient for forming an epitope recognizable by an antibody), a peptide which is a portion of a non-homologous region and consists of an amino acid sequence of 6 or more consecutive amino acids may be used in the present invention. For enhancing specificity, preferably a peptide which is a portion of a non-homologous region and consists of an amino acid sequence of 10 or more consecutive amino acids, or more preferably, 20 or more consecutive amino acids, may form an epitope.

Most preferably, a polypeptide encoded by AΔ6b-2# (P-AΔ6b-2#), a polypeptide encoded by CΔ6b-1b (P-CΔ6b-1b) and a polypeptide encoded by AΔ7b-1b (P-AΔ7b-1b), and a portion of a peptide consisting of a non-homologous region in the amino acid sequence encoded by A.pg-1.3 gene which may encompass the above polypeptides may be used. Besides, insofar that decreased sensitivity or increased non-specific reaction, which may interfere with detection of an antibody, is not provided, a mutated peptide may also be used where amino acid mutation is introduced. Two or more of these peptides may be used in combination therewith as occasion demands. For instance, when a causative agent of avian infectious coryza is to be identified, each of the respective peptides may preferably be used separately, or a mixture of A.pg-A-derived peptides or a mixture of A.pg-C-derived peptides may preferably be used separately. In case that merely epidemiology of avian infectious coryza infection or survey of efficacy of avian infectious coryza vaccine is aimed, a mixture of A.pg-A-derived peptides and a mixture of A.pg-C-derived peptides may further be mixed together for use.

Immunized sera after vaccination may be obtained by administering subcutaneously, intradermally or intraperitoneally a mixture of the above peptide and an adjuvant to an appropriate animal once to thrice at an interval of 2 to 4 weeks, taking blood subsequently from the animal and centrifuging blood (14,000 rpm, 5 minutes). Adjuvant may include Freund's complete adjuvant, Freund's incomplete adjuvant, aluminum hydroxide (e.g. ImjectAlum (Pearce)), and the like.

Similarly, sera of *Avibacterium paragallinarum*-infected animal may also be obtained by centrifuge of blood.

More specifically, any of various formats of ELISA may be conducted. For instance, a sample (immunized sera or A.pg-infected sera) may be initially added to a microtiter plate with an immobilized peptide, and after washing, a labeled anti-chicken antibody as a secondary antibody may be added to the plate. Alternatively, in combination with an antibody to a peptide-specific antibody, competitive ELISA may also be performed where a sample and a labeled anti-peptide (immobilized antigen) antibody are added simultaneously or separately or, in case that an anti-peptide antibody is not labeled, a labeled secondary antibody to an anti-peptide antibody is added.

Immobilization of a peptide on a microtiter plate may be carried out by letting the peptide left to stand at an amount of an antigen of 1-10 μg/ml at room temperature (around 25° C.) for 30 minutes to 2 hours or at a lower temperature (around 4° C.) for 12 to 24 hours. A blocking reagent for preventing a non-specific reaction may include Block Ace (SNOW BRAND MILK PRODUCTS CO., LTD.), blocking reagent for ELISA (Roche Diagnostics K.K.), a bovine serum albumin solution, a skim milk solution, and the like and may appropriately be selected. For washing after each of the reactions, PBS, TBS, or their mixture with Polysolbate (Tween 20) or a conservative (sodium azide) may be used and, for stopping the reaction, 2 to 3 molar sulfuric acid may be used. A secondary antibody may be an anti-chicken IgG labeled with HRP, fluorescent, RI or biotin. For instance, an anti-chicken IgG-HRP (Bethyl Laboratories, Inc.) as commercially available may be used. For instance, a substrate of HRP may include OPD (orthophenylenediamine) and TMBZ (3,3', 5,5'-tetramethylbendizine) where absorbance is measured at 492 nm and 450 nm, respectively.

ELISA by two-antibody sandwich may also be used where an antibody to a peptide is initially immobilized on a microtiter plate and the peptide is bound to said antibody. For this ELISA, either a polyclonal antibody or a monoclonal antibody to the peptide may be used. A polyclonal antibody may be obtained by the same procedure as described for immunized sera above. An animal for use in immunization may include chicken, rat, guinea pig, hamster, dog, monkey, and the like. A monoclonal antibody may be obtained by isolating antibody-producing cells such as splenocytes or lymphocytes from an animal immunized with A.pg cells or a polypeptide, and fusing these cells with myeloma cells in accordance with Milstein et al. (Method Enzymol., 73, 3-46, 1981) to prepare hybridomas producing an antibody to the peptide for use in the present invention. Also, a technique for preparing an antibody with the use of phage display library (Phage Display of Peptides and Proteins: A Laboratory Manual Edited by Brian K. Kay et al., Antibody Engineering: A PRACTICAL APPROACH Edited by J. McCAFFERTY et al., ANTIBODY ENGINEERING second edition edited by Carl A. K. BORREBAECK) may be utilized to prepare an antibody to the peptide for use in the present invention.

A method for measuring an anti-A.pg antibody by the thus established ELISA may be used for detecting an antibody induced by a vaccine or A.pg infection. The present invention is explained in more detail by means of the following Examples but should not be construed to be limited thereto.

Example 1

Preparation of A.pg-1.3 Gene and DNA Fragments within Region of Said Gene

Genomic DNA libraries were prepared from A.pg-A 221 strain and A.pg-C 53-47 strain in accordance with the method of Tokunaga et al. (Japanese Patent Publication No. 10-84969). Briefly, chromosomal DNAs were extracted from cells collected by centrifuge (8,000 rpm, 20 minutes) using SepaGene kit (Sanko Junyaku Co., Ltd.), and digested with restriction enzyme Sau3AI to prepare DNA libraries. Using DNA fragments from the DNA libraries as a template, PCR was performed with LA Taq (TAKARA BIO Inc.) in accordance with protocol attached thereto to amplify fragments each consisting of a portion of the A.pg-1.3 gene. PCR reaction was carried out with LA PCR kit vert (TAKARA SHUZO CO., LTD.) at 96° C. for 1 minute; then 30 cycles of at 96° C. for 40 seconds, at 56° C. for 60 seconds, and at 72° C. for 120 seconds; and at 72° C. for 10 minutes. FIG. 1 shows positional relationship of each of the DNA fragments. Amplification of each of the DNA fragments and primers used therefor are shown in Table 1 below. Each of the primers was added with a sequence for recognition by restriction enzyme.

TABLE 1

| DNA fragment | 5'-Primer | 3'-Primer |
|---|---|---|
| AΔ6b-1b | 5'AΔ6b-1b-P (SEQ ID NO: 5) | 3'AΔ6b-1b-P (SEQ ID NO: 6) |
| AΔ3-0 | 5'AΔ3-0-P (SEQ ID NO: 7) | 3'AΔ3-0-P (SEQ ID NO: 8) |
| AΔ5-0 | 5'AΔ5-0-P (SEQ ID NO: 9) | 3'AΔ5-0-P (SEQ ID NO: 10) |
| AΔ5-1 | 5'AΔ5-1-P (SEQ ID NO: 11) | 3'AΔ5-1-P (SEQ ID NO: 12) |
| CΔ6b-1b | 5'CΔ6b-1b-P (SEQ ID NO: 13) | 3'CΔ6b-1b-P (SEQ ID NO: 14) |
| CΔ5-1 | 5'CΔ5-1-P (SEQ ID NO: 15) | 3'CΔ5-1-P (SEQ ID NO: 16) |
| CΔ6-0 | 5'CΔ6-0-P (SEQ ID NO: 17) | 3'CΔ6-0-P (SEQ ID NO: 18) |
| AΔ6b-2# | 5'AΔ6b-2#-P (SEQ ID NO: 19) | 3'AΔ6b-2#-P (SEQ ID NO: 20) |
| AΔ7b-1b | 5'AΔ7b-1b-P (SEQ ID NO: 21) | 3'AΔ7b-1b-P (SEQ ID NO: 22) |

Example 2

Expression of Each of DNA Fragments

Figure 2:
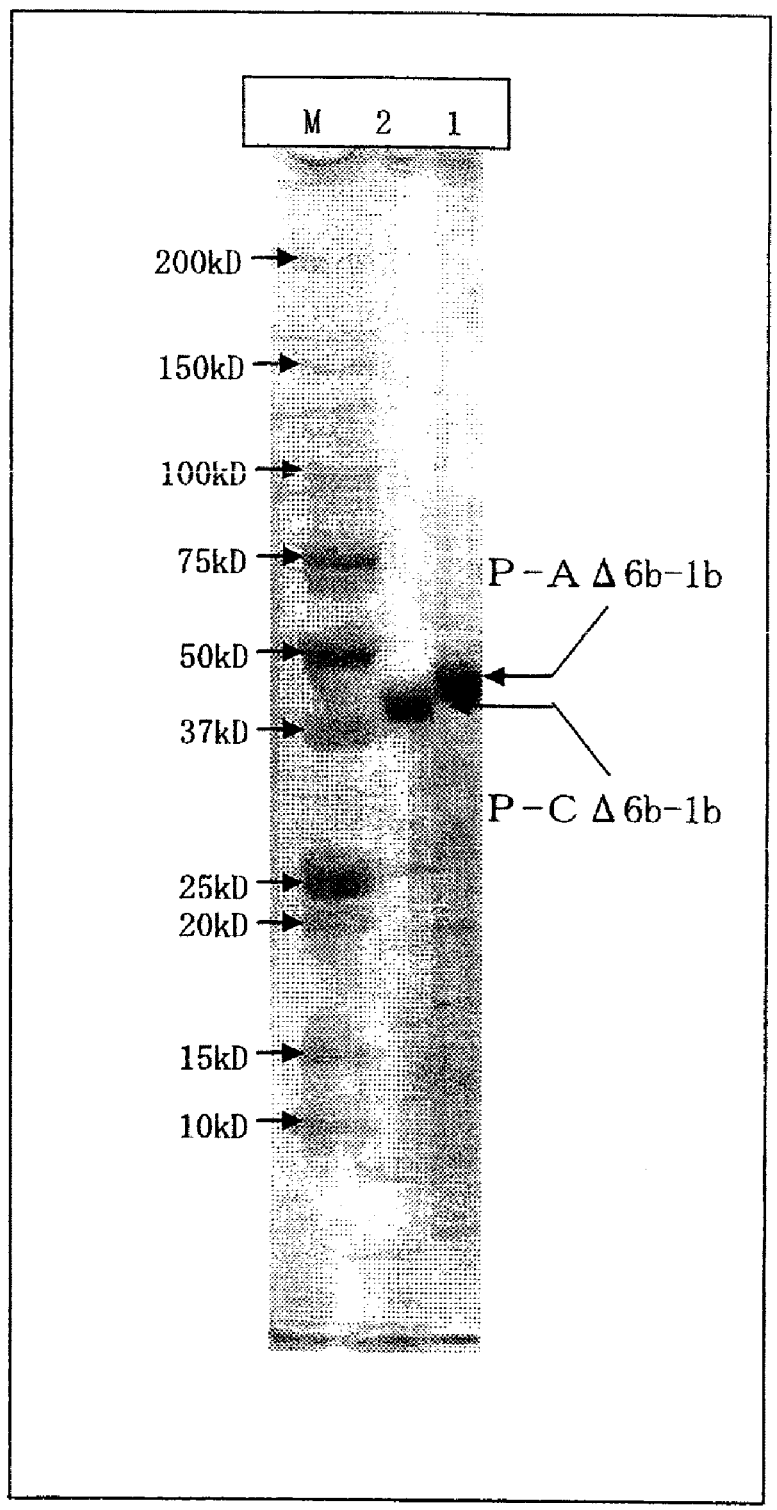
FIG. 2 shows the results of SDS-PAGE for each of the polypeptides purified from *E. coli*. M: Marker, Lane 1: P-AΔ6b-1b, Lane 2: P-CΔ6b-1b.

Each of the DNA fragments obtained in Example 1 was digested with suitable restriction enzymes and after separation on 0.8% agarose electrophoresis the amplified fragments were eluted and recovered with Quantum Prep Freeze N Squeeze DNA Gel Extraction Spin Co kit. The obtained fragments were ligated to plasmid pQE30 (QIAGEN: 6 His-tag sequences (SEQ ID NO: 23) are present immediate downstream the initiation codon) or pET22b, which has been digested with the same restriction enzymes as above and the 5'-end of which has been dephosphorylated. The resulting plasmids were used to transform *E. coli* JM109 strain. *E. coli* comprising the amplified fragments was cultured overnight in Circle Grow medium (Funakoshi Co., Ltd.) supplemented with ampicillin and on the next day IPTG was added at a final concentration of 1 mM for further culture for 2.5 hours. After centrifuge (10,000 rpm, 5 minutes), supernatant was discarded and precipitate was suspended in an amount of 1/10 relative to the culture of Lysis Buffer A (8 M urine, 100 mM NaH$_2$PO$_4$, 10 mM Tris, 10 mM Imidazole, pH 8.0) to dissolve the cells. After centrifuge (15,000 rpm, 15 minutes), supernatant of cell lysate was collected. The collected supernatant of cell lysate was mixed with 1 mL of Ni-NTA agarose gel for absorption to the gel and filled in a column attached with a bottom stopper. After washing the column, a fraction eluted with an eluate (8 M urine, 100 mM NaH$_2$PO$_4$, 10 mM Tris, 100 mM Imidazole, pH 8.0) was collected and sodium dodecyl sulfate polyacrylamide gel electrophoresis (SDS-PAGE) was conducted. Among the A.pg-A- and A.pg-C-derived fragments, FIG. 2 shows electrophoretic pattern of the expression products AΔ6b-1b and CΔ6b-1b which were used for ELISA antigen.

Example 3

Preparation of Anti-Polypeptide Chicken Sera

The polypeptide P-AΔ5-1 obtained in Example 2 was diluted with PBS to 10 μg/dose and added with aluminum hydroxide at a final concentration of 20%. The resultant mixture was administered subcutaneously to SPF chickens of 5 weeks old at the neck twice at an interval of 3 weeks for immunization. For the other polypeptides P-AΔ3-0, P-AΔ5-0, P-CΔ5-1 and P-CΔ6-0, they were diluted with PBS to 10 μg/dose and emulsified with an oil adjuvant (0.01 g antigen, 0.001 mL or less formalin, 0.01 mL Polysolbate 80, 0.04 mL sorbitan sesquioleate, 0.36 mL light liquid paraffin, the remainder phosphate buffer per dose (0.5 mL)) and the resultant mixture was once administered subcutaneously to SPF chickens of 5 weeks old at the neck. The chickens at 9-11 weeks old were bled to give immunized sera to each of the polypeptides.

Example 4

Confirmation of Reaction of Each Polypeptide with Immunized Sera by ELISA

The polypeptides P-AΔ6b-1b, P-AΔ6b-2#, P-AΔ7b-1b and P-CΔ6b-1b obtained in Example 2 were diluted with 50 mM bicarbonate buffer to 1.0-2.5 μg/mL and each 100 μL of the solution was added to 96-well plate for immobilization. After absorption at room temperature for 1 hour, the reaction solution was discarded, and the plate was washed with 200 μL of PBS-T (8.1 mM disodium hydrogenphosphate, 1.5 mM potassium dihydrogenphosphate, 137 mM sodium chloride, 2.7 mM potassium chloride, 0.05% Tween 20) and added with 200 μL of PBS-T supplemented with 5% skim milk for blocking. The blocking solution was discarded. Serum was diluted with PBS-T supplemented with 1% skim milk to 50- to 100-fold and each 100 μL of the solution was added to each well for reaction at room temperature for 1 hour. After removing the reaction solution, the plate was washed with PBS-T three times. An anti-chicken IgG-HRP-labeled antibody was diluted with PBS-T supplemented with 1% skim milk to 10,000- to 20.000-fold and each 100 μL of the solution was added to each well for reaction at room temperature for 1 hour in the dark. After removing the reaction solution, the plate was washed with PBS-T three times. Each 100 μL of a substrate solution (100 mM citrate, 200 mM disodium hydrogenphosphate, 0.004% orthophenylenediamine, hydrogen peroxide) was added for reaction at room temperature for 30 minutes. Each 100 μL of 3M sulfuric acid was added to stop the reaction. Absorbance at the wavelength of 492 nm was measured with 96-well plate reader (Molecular Devices Japan). The results are shown in Table 2.

TABLE 2

| | Immobilized antigen | | | |
|---|---|---|---|---|
| Chicken sera | P-AΔ6b-1b | P-AΔ6b-2# | P-AΔ7b-1b | P-CΔ6b-1b |
| Serum immunized with P-AΔ5-1 | 2.953 ± 0.032 | 1.642 ± 0.288 | 1.401 ± 0.136 | 0.045 ± 0.054 |
| Serum immunized with P-AΔ5-0 | 2.914 ± 0.030 | 2.697 ± 0.124 | 1.598 ± 0.261 | 0.043 ± 0.071 |
| Serum immunized with P-AΔ3-0 | 2.949 ± 0.041 | 2.742 ± 0.157 | 1.924 ± 0.193 | 0.043 ± 0.037 |
| Serum immunized with P-CΔ5-1 | 0.598 ± 0.515 | 0.032 ± 0.027 | 0.072 ± 0.015 | 1.153 ± 0.655 |
| Serum immunized with P-CΔ6-0 | 1.187 ± 0.798 | 0.074 ± 0.018 | 0.058 ± 0.019 | 2.003 ± 0.506 |
| Serum infected with A.pg-A | 1.068 ± 1.509 | 0.529 ± 0.708 | 0.648 ± 0.061 | 0.016 ± 0.004 |
| Serum infected with A.pg-A*[1] | ND*[2] | 0.417 ± 0.061 | ND | 0.123 ± 0.007 |
| Serum infected with A.pg-C*[1] | ND | 0.119 ± 0.009 | ND | 0.286 ± 0.067 |

Figures 3, 4:
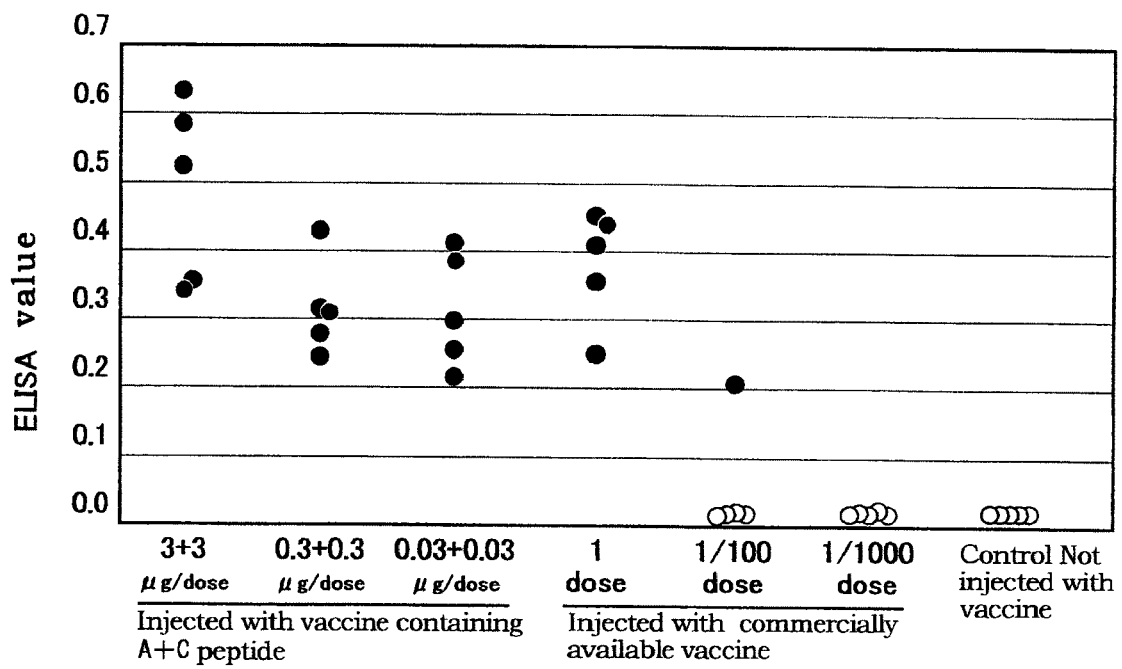
FIG. 3 shows homologous amino acid sequences and their positions in a non-homologous region of the amino acid sequence encoded by HMT p210 gene. The numbering of amino acid sequence in the figure corresponds to that of SEQ ID NO: 1 (A.pg-A) and of SEQ ID NO: 5 (A.pg-C) disclosed in Non-patent reference 2.
FIG. 4 shows correlation between ELISA value of serum before challenge with A.pg-A using the polypeptide P-AΔ6b-2# as an antigen and protection from onset of disease after challenge with A.pg-A. In the figure, ● shows chickens without onset of disease whereas ○ shows chickens with onset of disease.

*[1]Measured as described in Example 5 provided that serum was diluted to 100-fold and anti-chicken IgG-HRP-labeled antibody was diluted to 50,000-fold
*[2]Not done The polypeptide P-AΔ6b-1b which comprises an amino acid sequence homologous between the amino acid sequence of amino acids Nos. 243-271 of SEQ ID NO: 1 from Region 2 of A.pg-A and the amino acid sequence of amino acids Nos. 38-68 of SEQ ID NO: 2 from Region 2 of A.pg-C (among 31 amino acid residues, 30 amino acid residues are common; cf. FIG. 3) was reactive with any of sera immunized with the polypeptides (P-AΔ3-0, P-AΔ5-1, P-AΔ5-0, P-CΔ5-1 and P-CΔ6-0) which comprise Region 2. On the other hand, the polypeptides (P-AΔ6b-2#, P-AΔ7b-1b and P-CΔ6b-1b) which do not comprise the homologous amino acid sequence as described above were reactive in A.pg-A- or A.pg-C-specific manner. The polypeptides P-AΔ6b-2 and P-AΔ7b-1b also bound to sera infected with A.pg-A.

Example 5

Correlation Between Vaccinated Sera and Protection by ELISA

A commercially available oil adjuvant vaccine with an inactivated cell (Oilvacks 7; Juridical Foundation The Chemo-Sero-Therapeutic Research Institute) and a vaccine of the same composition as Oilvacks 7 excepting that A.pg antigen (inactivated A.pg-A and A.pg-C) was replaced with the polypeptides AΔ5-1 and CΔ5-1 obtained in Example 2 were prepared and subcutaneously injected once to SPF chickens of 5 weeks old at the neck. For the commercially available vaccine, in addition to 1 dose, its dilutions to 1/100 and 1/1,000 were also administered. For the polypeptides, a vaccine containing a mixture of the A.pg-A- and A.pg-C-derived polypeptides, each diluted to 3, 0.3 and 0.03 μg/chicken, was administered. After blood was taken from the chickens at 9 weeks old, 0.2 mL of a solution of A.pg-A 211 strain ($1.5 \times 10^9$ CFU/mL) or A.pg-C 53-47 strain ($5.0 \times 10^9$ CFU/mL) was administered intranasally to the chickens and clinical symptoms such as swelling of the face, a running nose and epiphora were observed for 1 week.

The obtained sera were subject to ELISA value as described below. The polypeptides P-AΔ6b-2# and P-CΔ6b-1b obtained in Example 2 were diluted with 50 mM bicarbonate buffer to 1.0 μg/mL and each 50 μL of the solution was added to 96-well plate for immobilization. After absorption at 4° C. overnight, the reaction solution was discarded, and the plate was washed with 300 μL of PBS-T (8.1 mM disodium hydrogenphosphate, 1.5 mM potassium dihydrogenphosphate, 137 mM sodium chloride, 2.7 mM potassium chloride, 0.05% Tween 20) and added with 300 μL of PBS-T supplemented with 5% skim milk for blocking. The blocking solution was discarded. Serum was diluted with PBS-T supplemented with 5% skim milk to 1,000-fold and each 50 μL of the solution was added to each well for reaction at room temperature for 1 hour. After removing the reaction solution, the plate was washed with PBS-T three times. An anti-chicken IgG-HRP-labeled antibody was diluted with PBS-T supplemented with 5% skim milk to 25,000-fold and each 50 μL of the solution was added to each well for reaction at room temperature for 30 minutes in the dark. After removing the reaction solution, the plate was washed with PBS-T three times. Each 100 μL of a substrate solution (TMB+substrate-chromogen; DAKO Corp.) was added for reaction at room temperature for 15 minutes. Each 100 μL of 3M sulfuric acid was added to stop the reaction. Absorbance at the wavelength of 450 nm was measured with 96-well plate reader (Molecular Devices Japan).

Figure 5:
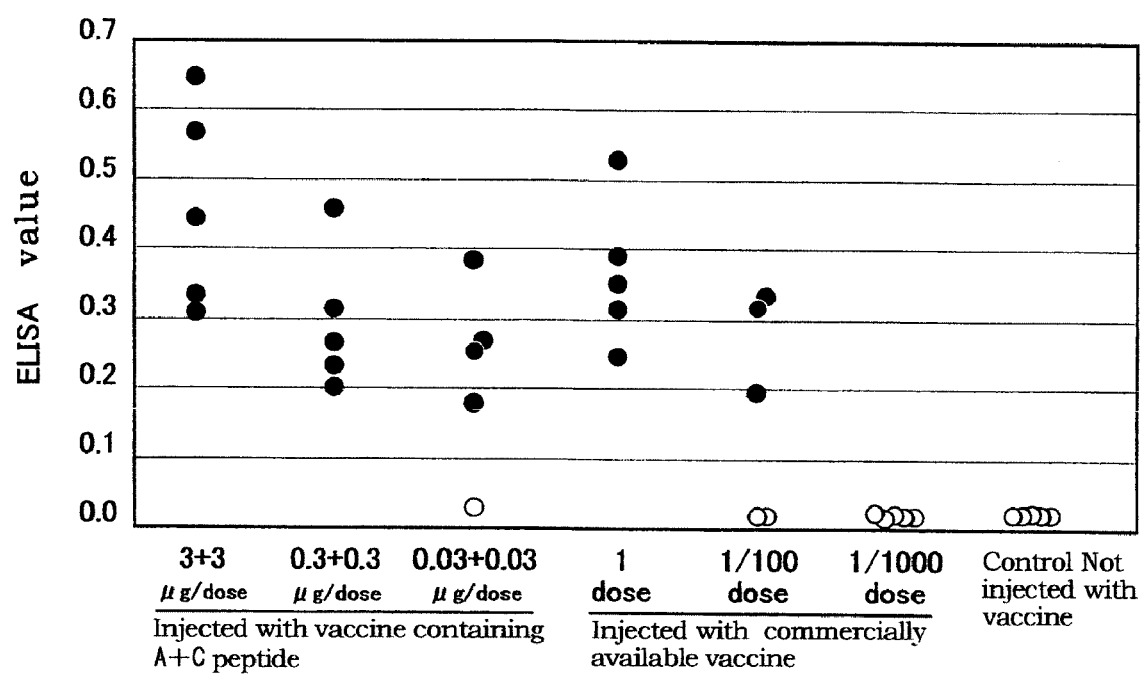
FIG. 5 shows correlation between ELISA value of serum before challenge with A.pg-C using the polypeptide P-CΔ6b-

As shown in FIGS. 4 and 5, for either chickens challenged with A.pg-A or A.pg-C, those chickens showing less than 0.1 of ELISA value in sera before challenge suffered from the disease to confirm infection. On the other hand, no chicken showing more than 0.1 of ELISA measurement in sera before challenge suffered from the disease. From these results, the use of ELISA system of the present invention would allow for estimation of a protection level of a vaccinal antibody.

INDUSTRIAL APPLICABILITY

The method for detection of the present invention may be used for testing immune condition of chickens immunized with a vaccine consisting of a polypeptide comprising the amino acid sequence as used in the present invention. Also, the method for detection of the present invention may be used for studying a mechanism of outbreak of disease or epidemiology by measuring sera from chickens suffering from avian infectious coryza through infection with A.pg.

---

The invention claimed is:

1. A method for detecting an antibody to *Avibacterium paragallinarum*, wherein said method comprises measuring an antibody in a sample by reacting the sample with at least one antigen of Peptide A or Peptide B below:
   wherein Peptide A consists of a portion of the amino acid sequence of SEQ ID NO: 1, consists of a peptide chain of 6 or more amino acid residues, and does not include amino acids Nos. 243-273 of SEQ ID NO: 1; and
   wherein Peptide B consists of a portion of the amino acid sequence of SEQ ID NO: 2, consists of a peptide chain of 6 or more amino acid residues, and does not include amino acids Nos. 38-68 of SEQ ID NO: 2.

2. The method of claim 1, wherein Peptide A or Peptide B is a peptide chain of 10 or more amino acid residues.

3. The method of claim 1, wherein Peptide A or Peptide B is a peptide chain of 20 or more amino acid residues.

4. The method of claim 1, wherein Peptide A consists of a portion of the amino acid sequence of SEQ ID NO: 1, comprises an amino acid sequence of amino acids Nos. 8-236 of SEQ ID NO: 1, and does not include amino acids Nos. 243-273 of SEQ ID NO: 1 or Peptide B consists of a portion of the amino acid sequence of SEQ ID NO: 2, comprises an amino acid sequence of amino acids Nos. 69-452 of SEQ ID NO: 2, and does not include amino acids Nos. 38-68 of SEQ ID NO: 2.

5. The method of claim 1, wherein Peptide A consists of amino acids Nos. 8-236 of SEQ ID NO: 1 or Peptide B consists of amino acids Nos. 69-452 of SEQ ID NO: 2.

6. The method of claim 4, comprising reacting at least one antigen of Peptide A with a sample, wherein Peptide A consists of a portion of the amino acid sequence of SEQ ID NO: 1, comprises an amino acid sequence of amino acids Nos. 274-445 of SEQ ID NO: 1, and does not include amino acids Nos. 243-273 of SEQ ID NO: 1.

7. The method of claim 5, comprising reacting at least one antigen of Peptide A with a sample, wherein Peptide A consists of amino acids Nos. 274-445 of SEQ ID NO: 1.

8. The method of claim 1, wherein the measuring the antibody is an assay selected from the group consisting of an enzyme-linked immunosorbent assay (ELISA), a Western blot, and a dot blot.

9. The method of claim 1, wherein the sample is sera from chickens infected with *Avibacterium paragallinarum* or sera from chickens to which an *Avibacterium paragallinarum* vaccine is administered.

10. A kit for measurement of an antibody to *Avibacterium paragallinarum* in a sample, comprising at least one antigen selected from the group consisting of Peptide A and Peptide B:
    wherein Peptide A consists of a portion of the amino acid sequence of SEQ ID NO: 1, consists of a peptide chain of 6 or more amino acid residues, and does not include amino acids Nos. 243-273 of SEQ ID NO: 1; and
    wherein Peptide B consists of a portion of the amino acid sequence of SEQ ID NO: 2, consists of a peptide chain of 6 or more amino acid residues, and does not include amino acids Nos. 38-68 of SEQ ID NO: 2.

11. The kit of claim 10, wherein Peptide A or Peptide B is a peptide chain of 10 or more amino acid residues.

12. The kit of claim 10, wherein Peptide A or Peptide B is a peptide chain of 20 or more amino acid residues.

13. The kit of claim 10, wherein Peptide A consists of a portion of the amino acid sequence of SEQ ID NO: 1, comprises an amino acid sequence of amino acids Nos. 8-236 of SEQ ID NO: 1, and does not include amino acids Nos. 243-273 of SEQ ID NO: 1 or Peptide B consists of a portion of the amino acid sequence of SEQ ID NO: 2, comprises an amino acid sequence of amino acids Nos. 69-452 of SEQ ID NO: 2, and does not include amino acids Nos. 38-68 of SEQ ID NO: 2.

14. The kit of claim 10, wherein Peptide A consists of an amino acid sequence of amino acids Nos. 8-236 of SEQ ID NO: 1 or Peptide B consists of an amino acid sequence of amino acids Nos. 69-452 of SEQ ID NO: 2.

15. The kit of claim 13, comprising Peptide A wherein Peptide A consists of a portion of the amino acid sequence of SEQ ID NO: 1, comprises an amino acid sequence of amino acids Nos. 274-445 of SEQ ID NO: 1, and does not include amino acids Nos. 243-273 of SEQ ID NO: 1.

16. The kit of claim 14, comprising Peptide A wherein Peptide A consists of amino acids Nos. 274-445 of SEQ ID NO: 1.

17. The kit of claim 10, further comprising one or more reagents for measuring the antibody selected from the group consisting of ELISA reagents, Western blot reagents, and dot blot reagents.

18. The kit of claim 10, wherein the sample is sera from chickens infected with *Avibacterium paragallinarum* or sera from chickens to which *Avibacterium paragallinarum* vaccine is administered.

* * * * *

SEQUENCE LISTING

```
<160> NUMBER OF SEQ ID NOS: 23

<210> SEQ ID NO 1
<211> LENGTH: 446
<212> TYPE: PRT
<213> ORGANISM: Avibacterium paragallinarum

<400> SEQUENCE: 1

Lys Gly Ile Tyr Leu Lys Ala Asp Gln Asn Asp Pro Thr Gly Asn Gln
1               5                   10                  15

Gly Gln Lys Val Glu Leu Gly Asn Ala Ile Thr Leu Ser Ala Thr Asn
            20                  25                  30

Gln Trp Ala Asn Asn Gly Val Asn Tyr Lys Thr Asn Asn Leu Thr Thr
        35                  40                  45

Tyr Asn Ser Gln Asn Gly Thr Ile Leu Phe Gly Met Arg Glu Asp Pro
    50                  55                  60

Ser Val Lys Gln Ile Thr Ala Gly Thr Tyr Asn Thr Thr Gly Asp Ala
65                  70                  75                  80

Asn Asn Lys Asn Gln Leu Asn Asn Thr Leu Gln Gln Thr Thr Leu Glu
                85                  90                  95

Ala Thr Gly Ile Thr Ser Ser Val Gly Ser Thr Asn Tyr Ala Gly Phe
            100                 105                 110

Ser Leu Gly Ala Asp Ser Val Thr Phe Ser Lys Gly Gly Ala Gly Thr
        115                 120                 125
```

```
Val Lys Leu Ser Gly Val Ser Asp Ala Thr Ala Asp Thr Ala Ala
        130                 135                 140
Thr Leu Lys Gln Val Lys Glu Tyr Arg Thr Thr Leu Val Gly Asp Asn
145                 150                 155                 160
Asp Ile Thr Ala Ala Asp Arg Ser Gly Gly Thr Ser Asn Gly Ile Thr
                165                 170                 175
Tyr Asn Leu Ser Leu Asn Lys Gly Thr Val Ser Ala Thr Glu Glu Lys
                180                 185                 190
Val Val Ser Gly Lys Thr Val Tyr Glu Ala Ile Arg Asn Ala Ile Thr
            195                 200                 205
Gly Asn Ile Phe Thr Ile Gly Leu Asp Asp Thr Thr Leu Asn Lys Ile
        210                 215                 220
Asn Asn Pro Ala Asp Gln Asp Leu Ser Asn Leu Ser Glu Ser Gly Lys
225                 230                 235                 240
Asn Ala Ile Thr Gly Leu Val Asp Val Val Lys Lys Thr Asn Ser Pro
                245                 250                 255
Ile Thr Val Glu Pro Ser Thr Asp Ser Asn Lys Lys Thr Phe Thr
                260                 265                 270
Val Gly Val Asp Phe Thr Asp Thr Ile Thr Glu Gly Asp Ala Thr Asp
            275                 280                 285
Asp Lys Lys Leu Thr Thr Ser Lys Ser Val Glu Ser Tyr Val Thr Asn
290                 295                 300
Lys Leu Ala Asn Phe Ser Thr Asp Ile Leu Leu Ser Asp Gly Arg Ser
305                 310                 315                 320
Gly Asn Ala Thr Thr Ala Asn Asp Gly Val Gly Lys Arg Arg Leu Ser
                325                 330                 335
Asp Gly Phe Thr Ile Lys Ser Glu Asn Phe Thr Leu Gly Ser Lys Gln
                340                 345                 350
Tyr Asn Gly Ser Asp Ser Leu Gly Val Met Tyr Asp Gln Asn Gly
            355                 360                 365
Val Phe Lys Leu Ser Leu Asn Met Thr Ala Leu Thr Thr Ser Leu Ala
        370                 375                 380
Asn Thr Phe Ala Lys Leu Asp Ala Ser Asn Leu Thr Asp Ser Asn
385                 390                 395                 400
Lys Glu Lys Trp Arg Thr Ala Leu Asn Val Tyr Ser Lys Thr Glu Val
                405                 410                 415
Asp Ala Glu Ile Gln Lys Ser Lys Val Thr Leu Thr Pro Asp Ser Gly
                420                 425                 430
Leu Ile Phe Ala Thr Lys Gln Ala Gly Ser Gly Asn Asn Ala
        435                 440                 445

<210> SEQ ID NO 2
<211> LENGTH: 453
<212> TYPE: PRT
<213> ORGANISM: Avibacterium paragallinarum

<400> SEQUENCE: 2

Lys Leu Ile Ser Leu Ser Ala Thr Glu Glu Glu Val Val Ser Gly
1               5                   10                  15
Glu Ala Val Tyr Asp Ala Leu Lys Gly Ala Lys Pro Thr Val Ser Ala
                20                  25                  30
Glu Ala Asn Lys Gly Ile Thr Gly Leu Val Asp Val Val Lys Lys Ala
            35                  40                  45
Asn Ser Pro Ile Thr Val Glu Pro Ser Thr Asp Asn Asn Lys Lys Lys
        50                  55                  60
```

```
Thr Phe Thr Val Gly Leu Met Lys Asp Ile Glu Gly Val Asn Ser Ile
 65                  70                  75                  80

Thr Phe Asp Lys Ser Gly Gln Asp Leu Asn Gln Val Thr Gly Arg Met
                 85                  90                  95

Ser Ser Ala Gly Leu Thr Phe Lys Lys Gly Asp Thr Thr Asn Gly Ser
            100                 105                 110

Thr Thr Thr Phe Ala Glu Asp Gly Leu Thr Ile Asp Ser Thr Thr Asn
        115                 120                 125

Ser Ala Gln Thr Asn Leu Val Lys Val Ser Arg Asp Gly Phe Ser Val
130                 135                 140

Lys Asn Gly Ser Asp Glu Ser Lys Leu Ala Ser Thr Lys Leu Ser Ile
145                 150                 155                 160

Gly Ala Glu Asn Ala Glu His Val Glu Val Thr Lys Ser Gly Ile Ala
                165                 170                 175

Leu Lys Ala Asp Asn Thr Ser Asp Lys Ser Ile Thr Leu Ala Gln
            180                 185                 190

Asp Ala Ile Thr Leu Ala Gly Asn Ala Thr Gly Thr Ala Ile Lys Leu
        195                 200                 205

Thr Gly Val Ala Asp Gly Asn Ile Thr Val Asn Ser Lys Asp Ala Val
210                 215                 220

Asn Gly Gly Gln Leu Arg Thr Leu Leu Gly Val Asp Ser Gly Ala Lys
225                 230                 235                 240

Ile Gly Gly Thr Glu Lys Thr Thr Ile Ser Glu Ala Ile Ser Asp Val
                245                 250                 255

Lys Gln Ala Leu Thr Asp Ala Thr Leu Ala Tyr Lys Ala Asp Asn Lys
            260                 265                 270

Asn Gly Lys Thr Val Lys Leu Thr Asp Gly Leu Asn Phe Thr Ser Thr
        275                 280                 285

Thr Asn Ile Asp Ala Ser Val Glu Asp Asn Gly Val Val Lys Phe Thr
290                 295                 300

Leu Lys Asp Lys Leu Thr Gly Leu Lys Thr Ile Ala Thr Glu Ser Leu
305                 310                 315                 320

Asn Ala Ser Gln Asn Ile Ile Ala Gly Gly Thr Val Thr Val Gly Gly
                325                 330                 335

Glu Thr Glu Gly Ile Val Leu Thr Lys Ser Gly Ser Gly Asn Asp Arg
            340                 345                 350

Thr Leu Ser Leu Ser Gly Ala Gly Asn Ala Ala Thr Asp Gly Ile Lys
        355                 360                 365

Val Ser Gly Val Lys Ala Gly Thr Ala Asp Thr Asp Ala Val Asn Lys
370                 375                 380

Gly Gln Leu Asp Lys Leu Phe Lys Ala Ile Asn Asp Ala Leu Gly Thr
385                 390                 395                 400

Thr Asp Leu Ala Val Thr Lys Asn Pro Asn Gln Thr Ser Ile Phe Asn
                405                 410                 415

Pro Ile Asn Gly Thr Ala Pro Thr Thr Phe Lys Asp Ala Val Asp Lys
            420                 425                 430

Leu Thr Thr Ala Val Asn Thr Gly Trp Gly Ser Lys Val Gly Ile Leu
        435                 440                 445

Ala Thr Gly Ile Asp
    450

<210> SEQ ID NO 3
<211> LENGTH: 1338
<212> TYPE: DNA
<213> ORGANISM: Avibacterium paragallinarum
```

-continued

<400> SEQUENCE: 3
aaagggatct accttaaagc ggatcagaat gatccaacag gaaatcaagg tcagaaagtg 60
gaacttggta atgcaataac gctttcggca acaaatcaat gggcgaataa cggcgtaaat 120
tataaaacga acaatttaac cacttataat tcacaaaatg gcacgatttt atttggaatg 180
cgtgaagatc caagtgtaaa acaaattaca gcgggaacct ataatacaac gggtgatgcg 240
aacaataaaa atcaactaaa taatacactt caacaaacca cgcttgaagc aactgggatc 300
accagtagcg taggttcaac taactacgct ggctttagct taggggcaga cagcgtcacc 360
ttctcgaaag gtggagctgg cacggtgaaa ctttctggcg taagcgatgc cacagccgac 420
accgacgctg ccactctaaa acaagtgaaa gaataccgca caacattagt gggtgataat 480
gacatcaccg cagcagatcg tagtggcggc acaagcaatg gcattaccta caacttaagc 540
cttaataaag gtacggtttc ggcaacagaa gaaaaagtgg tgtcagggaa aactgtctat 600
gaagccatta gaaatgccat cacaggcaac atcttcacaa ttggcttaga cgataccacc 660
ttgaacaaaa tcaacaatcc cgcggatcaa gatctttcaa acctcagtga aagtggcaaa 720
aatgccatta cgggcttagt ggatgtggtg aaaaaaacaa attcaccgat cacagttgag 780
ccttctaccg atagcaacaa gaaaaaaacc ttcactgtag gcgtggattt caccgatacc 840
attacggaag gtgacgcaac ggatgataaa aaactgacga cttcaaaatc cgttgaaagc 900
tatgtcacaa acaaactcgc gaacttctct acagatattt tgttatcgga tgggcgttct 960
ggtaacgcaa caacggcaaa tgatggggtg ggtaaacgtc gtttgtctga tggctttacg 1020
atcaaatctg aaaactttac gctaggttca aaacaatata atggctctga tagcttaggg 1080
gtaatgtatg acgatcaaaa tggggtcttt aaattaagcc taaatatgac cgcacttacc 1140
acttcattgg ctaatacttt cgcgaagttg gatgcctcta accttactga tgatagcaat 1200
aaagagaaat ggcgtactgc gttgaatgtg tattcaaaaa cagaagtaga tgcagaaatt 1260
caaaaatcca aggtaacact cacaccagat tcgggtttga tctttgcgac caaacaagct 1320
gggagtggta ataacgca 1338

<210> SEQ ID NO 4
<211> LENGTH: 1359
<212> TYPE: DNA
<213> ORGANISM: Avibacterium paragallinarum

<400> SEQUENCE: 4
aaattgatct cgctttcggc aacagaagaa gaagaagtgg tgtcagggga agctgtctat 60
gatgcactta aaggtgcaaa accaacggtt tcagcagaag ccaacaaagg cattactggc 120
ttggtggatg tggtgaaaaa agcaaattca ccgatcacag ttgagccttc taccgataac 180
aacaagaaaa aaaccttcac tgtcggctta atgaaagaca ttgaaggggt aaacagcatt 240
acctttgata agtcagggca agatctaaat caagttacgg gcagaatgag cagtgcgggt 300
ttaaccttca aaaaaggcga cacaacaaat ggttcaacca ccacttttgc agaagatggc 360
ttaaccattg atagcacaac aaattctgct caaacaaact tagtgaaagt aagtcgtgat 420
ggcttctcgg tgaaaaatgg cagcgatgaa agcaaattag cctcgacaaa attatctatc 480
ggtgcggaaa atgcagaaca cgttgaagta actaaatcgg gcatagcctt aaaagcggat 540
aacacctccg ataaatctag catcacctta gcccaagatg cgattactct tgcggggaac 600
gcaaccggaa cggcgattaa attgactggt gttgcagatg gcaacattac ggtaaattca 660
aaagatgcgg taaatggggg gcagttgcgt accttattag ggttgatag cggggctaaa 720

```
attggcggta ctgagaaaac aacgatcagt gaagccattt ctgatgtgaa gcaagctctt      780
accgatgcga cattggcata taaagcggac aataaaaacg gtaaaacagt taaattgact      840
gacggattga attttactag cacgaccaat attgatgctt cagtggaaga taacggtgtg      900
gtgaaattca ccttaaaaga taaattaaca ggcttaaaaa ctatcgcaac tgaatctttg      960
aatgcttctc aaaatatcat cgctggcggt acggtaacag tgggcggcga cacagagggc     1020
attgtgctaa caaaatctgg ctcaggaaat gaccgcactt tatctttatc tggtgcaggc     1080
aatgcagcaa cagatggcat taaagtctct ggcgtgaaag cagggacggc agacaccgat     1140
gcggtgaata aggtcagtt agataaactt tttaaagcga tcaatgacgc attaggcaca      1200
acagatttag cggtaaccaa aaatccaaat caaacctcta tctttaatcc gataaacggc     1260
acggctccaa ccacctttaa agacgcggtg gataattaa ccaccgctgt gaatacaggt      1320
tggggatcaa aggtaggtat tttggcaaca ggtattgat                             1359
```

```
<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcggatccg atcagaatga tccaacagga aatcaa                               36

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgcgtcgac gttattacca ctcccagctt gtttg                                35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catgccatgg tttatgatga aactactcga gccttt                               36

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcggatcct taaggctaaa aaaagctaaa tccaacactc at                        42

<210> SEQ ID NO 9
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
catgccatgg atggcacaat tacatttaca aatatt                                    36

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcggatcct taaggctaaa aaaagctaaa tccaacactc at                              42

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catgccatgg atggcacaat tacatttaca aatatt                                    36

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgcgtcgac accttgagtg ctagatgctg taggtgc                                   37

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgcggatccg gcttaatgaa agacattgaa ggggtaaac                                  39

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgcgtcgac aatacctgtt gccaaaatac ctacctttga                                40

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 15
catgccatgg atggcacaat tacatttaca aatatt                                      36

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcggatccc ataccttgag tgctagatgc tgtaggtgc                                   39

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catgccatgg atgcgattaa taatgttctc ac                                          32

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcggatcct taaggctaaa aaaagctaaa tccaacactc at                               42

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgcggatccg atcagaatga tccaacagga aatcaa                                      36

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgcgtcgac actgaggttt gaaagatctt gat                                         33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 21
cgcggatccg gcgtggattt caccgatacc att                                33

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgcgtcgac gttattacca ctcccagctt gtttg                              35

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```